(12) United States Patent
Letellier et al.

(10) Patent No.: US 12,383,642 B2
(45) Date of Patent: Aug. 12, 2025

(54) METHOD FOR DECONTAMINATING A PREFORM WITH REACTIVE SPECIES OBTAINED BY MIXING A PRECURSOR AGENT AND A PLASMA

(71) Applicant: SIDEL PARTICIPATIONS, Octeville-sur-Mer (FR)

(72) Inventors: Sandy Letellier, Octeville-sur-Mer (FR); Grégory Toutain, Octeville-sur-Mer (FR); Foune Seck, Octeville-sur-Mer (FR)

(73) Assignee: SIDEL PARTICIPATIONS, Octeville-sur-Mer (FR)

( * ) Notice: Subject to any disclaimer, the term of this patent is extended or adjusted under 35 U.S.C. 154(b) by 722 days.

(21) Appl. No.: 17/625,475

(22) PCT Filed: Jul. 9, 2020

(86) PCT No.: PCT/EP2020/069335
§ 371 (c)(1),
(2) Date: Jan. 7, 2022

(87) PCT Pub. No.: WO2021/005144
PCT Pub. Date: Jan. 14, 2021

(65) Prior Publication Data
US 2022/0288255 A1    Sep. 15, 2022

(30) Foreign Application Priority Data

Jul. 11, 2019    (FR) ...................................... 1907781

(51) Int. Cl.
*A61L 2/14*        (2006.01)
*A61L 2/20*        (2006.01)
(Continued)

(52) U.S. Cl.
CPC ................. *A61L 2/14* (2013.01); *A61L 2/208* (2013.01); *A61L 2/26* (2013.01);
(Continued)

(58) Field of Classification Search
CPC ......... A61L 2/14; A61L 2/208; A61L 2202/23
See application file for complete search history.

(56) References Cited

U.S. PATENT DOCUMENTS

2012/0294760 A1* 11/2012 Humele ................... A61L 2/10
422/186.05
2013/0142694 A1    6/2013 Krohmann
2018/0296714 A1   10/2018 Higashiyama et al.

FOREIGN PATENT DOCUMENTS

IT    102012902068594 A1    1/2014
IT    RM20120334        *    1/2014
(Continued)

OTHER PUBLICATIONS

International search report dated Sep. 22, 2020.

*Primary Examiner* — Donald R Spamer
*Assistant Examiner* — Kayla Rose Sarantakos
(74) *Attorney, Agent, or Firm* — Blake T. Hudson; Stephanie Davy-Jow

(57) ABSTRACT

The invention relates to a method for decontaminating a preform made of thermoplastic material by exposing at least part of the preform to reactive species obtained by mixing a precursor agent with a plasma, the plasma being generated by injection of a carrier gas into a reactor, the method including mixing of the precursor agent with the plasma is carried out exclusively outside the reactor before it is in contact with the preform. The invention also relates to a decontamination device for carrying out the method.

16 Claims, 2 Drawing Sheets

(51) Int. Cl.
  *A61L 2/26* (2006.01)
  *B29C 49/42* (2006.01)
  *H05H 1/24* (2006.01)
(52) U.S. Cl.
  CPC ..... *B29C 49/42418* (2022.05); *H05H 1/2406* (2013.01); *A61L 2202/11* (2013.01); *A61L 2202/15* (2013.01); *A61L 2202/23* (2013.01); *H05H 1/47* (2021.05)

(56) References Cited

FOREIGN PATENT DOCUMENTS

| IT | RM20120334 A1 | 1/2014 |
| WO | WO2011138463 A1 | 11/2011 |
| WO | 2011149188 A2 | 12/2011 |
| WO | WO2017218832 A1 | 12/2017 |
| WO | WO2019084203 A1 | 5/2019 |

\* cited by examiner

Fig. 3
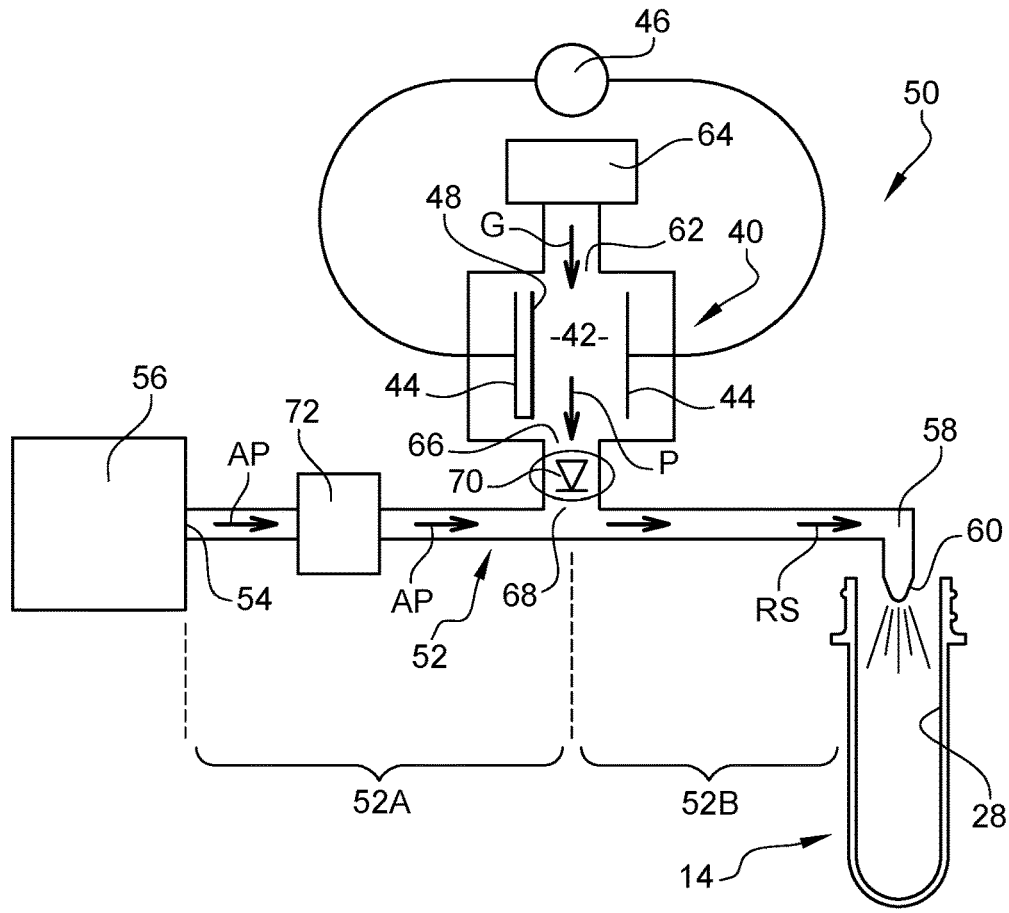
Fig. 5
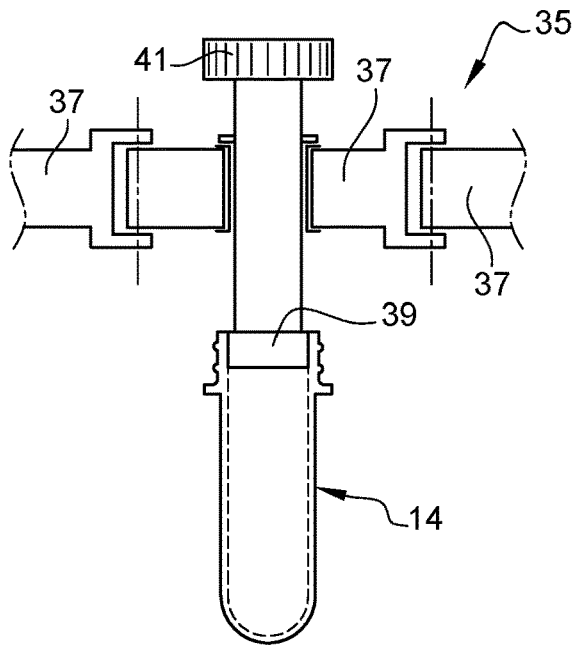
Fig. 6

METHOD FOR DECONTAMINATING A PREFORM WITH REACTIVE SPECIES OBTAINED BY MIXING A PRECURSOR AGENT AND A PLASMA

TECHNICAL FIELD OF THE INVENTION

The invention relates to a method for decontaminating a preform of thermoplastic material by exposing at least part of the preform to reactive species obtained by mixing a precursor agent with a plasma, the plasma being generated by injecting a carrier gas into a reactor.

TECHNICAL BACKGROUND

In the field of food packaging, it is known to carry out a decontamination treatment for disinfecting or sterilizing at least certain parts of a container intended to receive foodstuffs, in particular the interior and the neck of the container.

The decontamination treatments applied aim to destroy or at least reduce the presence of microbiological organisms or microorganisms, such as in particular microbes, bacteria, spores, molds, etc. in order to allow preservation of the products. "Container" means a hollow body such as for example a bottle, a flask, a pot, etc., all of which are containers obtained by transformation of a thermoplastic preform, which most often is manufactured beforehand by injection molding. The preform comprises in particular a body that is intended to be formed to its final shape in a manufacturing process, and it also comprises a neck, which already has its final form.

Of the thermoplastics, PET (polyethylene terephthalate) is the most commonly used for these applications.

During manufacture of the container, the body of the preform is first conditioned thermally in a furnace in order to soften its constituent material. For this purpose, the furnace comprises heating devices, in particular by emission of heating electromagnetic radiation, for example by infrared lamps. Softened in this way, the preform is then transformed into a container by blowing in a mold by means of at least one fluid under pressure, with or without drawing. The neck of the preform is kept at a sufficiently cold temperature so that it is not deformed during the container manufacturing process.

As a variant, the injection-molded preform is transformed into a container directly without in that case requiring preliminary thermal conditioning.

In the prior art, decontamination of a preform is carried out in particular by a "chemical route" by means of a sterilizing agent comprising hydrogen peroxide ($H_2O_2$) or some other product with similar properties, i.e. bactericide, virucide, fungicide, etc. It is more particularly a so-called "precursor" agent, which can be decomposed into reactive species, and in particular into reactive oxygen species (ROS). The reactive oxygen species comprise in particular hydroxyl radicals, superoxide anions, hydroxyl ions, etc. Bacteria and viruses are destroyed very effectively by contact with reactive oxygen species.

Decomposition of the precursor agent into reactive oxygen species is carried out for example by heating the precursor agent to a high temperature for at least a defined minimum duration. Sterilization with reactive oxygen species is extremely effective. It is, moreover, particularly harmless for consumers since the final residues of the chemical reactions consist only of water and dioxygen.

Thus, injection of a precursor agent, such as a solution of hydrogen peroxide and water, in the vapor state into a preform before it goes into the furnace, is already known. The vapor condenses on contact with the inside wall of the preform. Then, as the preform goes into the furnace, the condensed precursor agent is heated at the same time as the body of the preform by the heating devices of the furnace. The heat is generally sufficient for partially decomposing the precursor agent contained in the preform.

The preform thus contains a sterilizing atmosphere throughout the manufacture of the container until the container is filled. However, the amount of heat received by the precursor agent contained in the preforms while they are heated is not generally sufficient to decompose all the precursor agent into reactive oxygen species. The amount of heat transmitted to the preforms depends for example on the size of the preforms, the shape of the final container, the color of the preforms, etc.

To solve this problem, it is possible to heat the preforms in the furnace for longer than necessary so that most of the precursor agent is decomposed into reactive oxygen species.

However, it is not always possible to heat the precursor agent sufficiently without degrading the preforms.

Furthermore, the need to continue to heat the preforms although their body has already reached the desired temperature for shaping to the final container leads to an increase in the manufacturing cost of the containers.

Moreover, although the residues from reaction of the reactive oxygen species are harmless, the precursor agent, in particular hydrogen peroxide, may be toxic above a certain dose. This may pose a problem, especially when the container is intended to contain foodstuffs. For this reason, certain countries impose draconian standards for the residual quantity of precursor agent permitted in a container after filling. For example, the container must contain less than 0.5 ppm of precursor agent.

To achieve this objective, and bearing in mind the heating problems mentioned above, it is sometimes necessary to dilute the precursor agent in a harmless solvent, for example water, to reduce the amount of precursor agent injected into the container. However, with a lower content of precursor agent, the efficacy of the sterilizing treatment may be reduced considerably.

It has already been proposed to decompose the precursor agent by means of a plasma. For this purpose, it is known to inject the precursor agent mixed with a carrier gas, such as air, into a capacitive plasma reactor. A reactor of this kind comprises a reaction chamber containing two electrodes, between which a large potential difference is applied. This causes ionization of the carrier gas that activates the decomposition of the precursor agent into reactive oxygen species. This solution advantageously makes it possible to decompose almost all of the precursor agent into reactive oxygen species even before being brought into contact with the object to be decontaminated.

It is already known that the carrier gas decomposes at least partly into reactive species. However, owing to the presence of the precursor agent, the concentration of reactive species becomes extremely high. The reaction chamber then has a high concentration of reactive oxygen species. These elements, in particular the hydroxyl ion, have very strong oxidizing power and consequently are particularly corrosive. No matter what material they are made of, the electrodes are therefore consumed rapidly and must be replaced very frequently.

SUMMARY OF THE INVENTION

The invention proposes a method for decontaminating a preform of thermoplastic material by exposing at least part of the preform to reactive species obtained by mixing a precursor agent with a plasma, the plasma being generated by injecting a carrier gas into a reactor.

The method of the invention is characterized in that the mixing of the precursor agent with the plasma is carried out exclusively outside of the reactor before it is in contact with the preform. Thus, the electrodes of the reactor are never in contact with the precursor agent or with the reactive species obtained by decomposition of the precursor agent in contact with the plasma. According to other characteristic features of the method of the invention:

- at least one internal face (28) of the preform is exposed to the reactive species, the reactive species being confined within the preform for a length of time determined by the confinement means;
- the method is carried out while the preform is transported through a plant for manufacturing containers starting from preforms comprising a furnace for heating the preforms, the reactive species being injected into the preform before or during heating thereof in the heating furnace, the reactive species being confined in the preform until it leaves the heating furnace;
- the reactive species are confined in the preform by a confinement means which will be fixed inside the neck of the preform;
- the reactive species are confined in the preform by a confinement means which will be fixed outside the neck of the preform.

This confinement means fixed inside or outside the neck makes it possible to isolate the interior of the preform with respect to its external environment.

- the reactive species are confined in the preform by means of a mandrel that grips the preform by its neck so that it can be moved in the heating furnace;
- the precursor agent is mixed with the plasma at discharge from the reactor;
- the precursor agent comprises hydrogen peroxide;
- the precursor agent is in the vapor state when it is mixed with the plasma;
- the precursor agent is in the form of mist when it is mixed with the plasma;
- the carrier gas is formed by dioxygen;
- the carrier gas is air;
- the reactive species comprise one or more of the following chemical elements:
  reactive oxygen species (ROS);
  reactive nitrogen species (RNS);
  ozone ($O_3$).

The invention also relates to a decontamination device for applying the method of decontamination implemented according to the teachings of the invention.

The decontamination device is characterized in that it comprises:

- a decontamination line, an upstream end of which is connected to a source of precursor agent and a downstream end of which is connected to at least one injection nozzle intended to project, onto at least part of the preform, the reactive species obtained by decomposition of the precursor agent at the time of mixing with the plasma;
- a plasma reactor that is connected to a source of carrier gas and an outlet of which is connected to the decontamination line by a branch pipe that splits the decontamination line into an upstream section in which the undecomposed precursor agent is intended to circulate, and a downstream section in which the reactive oxygen species produced by the decomposition of the precursor agent at the time of mixing with the plasma are intended to circulate.

According to other characteristic features of the decontamination device of the invention:

- the plasma reactor is a cold plasma reactor such as a corona discharge reactor or a dielectric barrier discharge reactor;
- the decontamination line comprises an evaporator of the precursor agent, which is arranged upstream of the branch pipe with the plasma reactor;
- the decontamination line comprises a precursor agent misting device, which is arranged upstream of the branch pipe.

BRIEF DESCRIPTION OF THE FIGURES

Other features and advantages of the invention will become clear on reading the detailed description given hereunder, for understanding of which reference will be made to the appended drawings, in which:

FIG. 3 is a schematic view showing a decontamination device designed for applying the method of decontamination implemented according to the teachings of the invention;

FIG. 5 is an axial sectional view which shows schematically a part of a conveyor chain comprising a rotating plate transporting a preform through the heating furnace;

FIG. 6 is a side view that shows schematically a preform exposed to a laminar air flow that is able to confine reactive species contained in the preform.

DETAILED DESCRIPTION OF THE INVENTION

In the rest of the description, elements having an identical structure or similar functions will be denoted by one and the same reference symbol.

Figure 1:
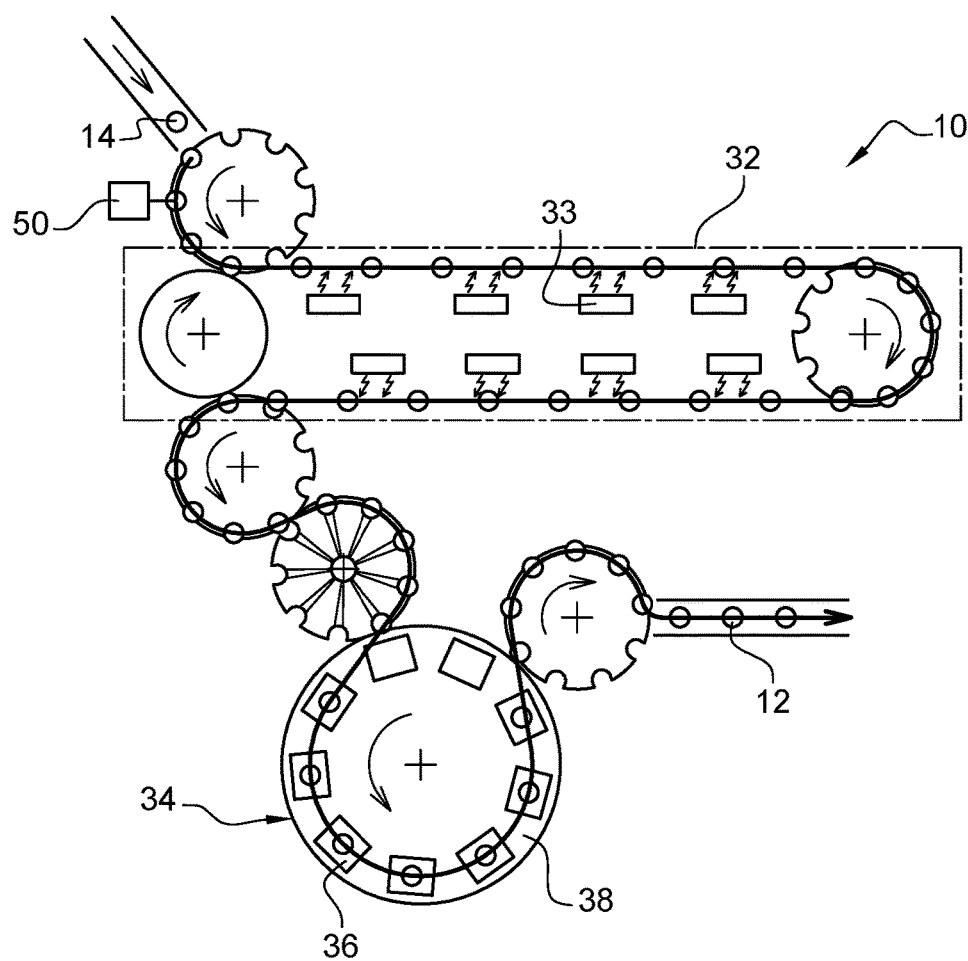
FIG. 1 is a schematic top view showing an example of a plant for making containers by molding preforms, which is equipped with a decontamination device implemented according to the teachings of the invention.

FIG. 1 shows a plant 10 for mass production of containers. Said plant 10 makes it possible to manufacture final containers 12 by molding preforms 14.

Figure 2:
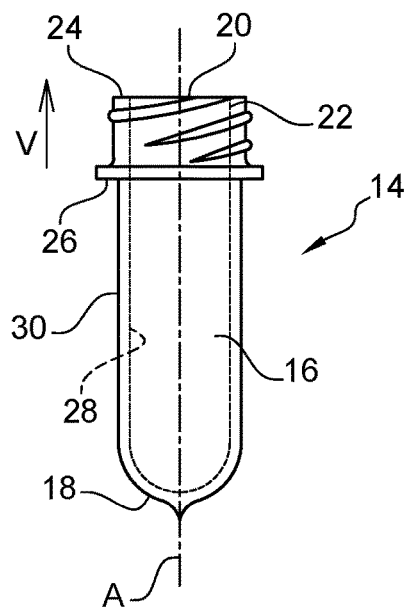
FIG. 2 is a side view showing an example of preform that can be decontaminated by application of the method carried out according to the teachings of the invention.

FIG. 2 illustrates an example of a preform 14 made of thermoplastic material. Here, the preform 14 is made of polyethylene terephthalate (PET).

Said preform 14 is generally obtained by injection molding of plastic and has characteristics (dimensions, distribution of material, etc.) that are determined by the final container 12 to be obtained, in particular its shape or its capacity.

The preform 14 has an axisymmetric shape with a principal axis "A", shown vertically in FIG. 2. The preform 14 comprises in particular a tubular body 16 closed at a lower end by a bottom 18 and that is open at the top with an upper opening 20 delimited radially by a neck 22. The principal axis "A" of the preform 14 passes through the middle of the neck 22.

The neck 22 of the preform 14 has its definitive form at the end of manufacture by injection molding of the preform 14 and corresponds to the neck of the final container 12. An edge 24 of the upper free end of the neck 22, also called lip, delimits circumferentially the circular opening 20 constituting the only access to the interior of the preform 14.

In the example shown in FIG. 2, the neck 22 comprises a flange 26, which extends radially, projecting outwards.

The body 16 is delimited by a tubular wall, which has an internal face 28 located inside the preform 14, shown with dashed lines in FIG. 2, and an external face 30 located on the outside.

The preform 14 has for example an opening 20 with inside diameter of about 20 mm and a total height of about 90 mm. The thickness of the wall delimiting the body 16 is for example about 3 mm. These values are given as nonlimiting examples; the preforms 14 may have different dimensions while maintaining identical overall proportions.

Referring again to FIG. 1, the manufacturing plant 10 mainly comprises a heating furnace 32, which comprises devices 33 for heating the body 16 of the preforms 14 above a glass transition temperature at which the material becomes malleable. To ensure that the neck 22 of the preforms 14 is not deformed during the manufacturing process, the furnace 32 comprises means for keeping the temperature of the neck 22 below its glass transition temperature.

The heating furnace 32 comprises a device 35 for conveying the preforms 14 in a row. The conveying device 35 comprises individual supports circulating in a closed circuit in the heating station 10.

Figure 4:
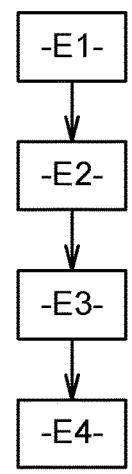
FIG. 4 is a block diagram of the method of decontamination implemented according to the teachings of the invention.

In the embodiment shown in FIGS. 2 to 4, the conveying device 35 comprises in this case a plurality of transporting elements 37 forming the links of a closed transport chain. Each transporting element 37 carries at least one individual support. Each individual support comprises a mandrel 39. The mandrel 39 is intended to be fitted into the neck of a preform 14. According to a known embodiment example, the mandrel 39 is provided with elastic means (not shown), such as an O-ring seal, advantageously made of an elastic material (such as an elastomer), and whose outside diameter is equal to or slightly greater than the inside diameter of the neck of a preform 14, so as to provide lifting of the preform 14 by friction against the inside wall of the neck, when the mandrel 39 has been inserted, and to isolate the interior of the preform from its external environment, thus guaranteeing the quality of decontamination.

In general, each mandrel 39 comprises means, such as a pinion 41 interacting with a fixed belt (not shown), capable of causing the preform 14 to rotate about its principal axis during its displacement along at least part of the transport path to allow uniform heating of the body of the preform 14. A transport device of this kind with a rotating mandrel 39 is sometimes called "rotating plate".

The manufacturing plant 10 also comprises a blowing station 34, which comprises molding units 36 for receiving the preforms 14. The preforms 14 are intended for example to be formed into final containers 12 by drawing and blowing in a mold (not shown) of a molding unit 36. The molding units 36 are mounted on a carrousel 38, which allows the preforms 14 to be moved during their transformation into final containers 12 from an inlet point to an outlet point.

During the manufacturing process, the preforms 14, and then the containers 12, are moved in a row along a defined production path, shown with a thick line in FIG. 1, by conveyors. The conveyors comprise individual means of support (not shown) for each hollow body in the state of a preform 14 or a container 12. These conveyors are well known in the prior art and will not be described in detail here.

Manufacture of the containers 12 is not carried out in a clean room, even when they are intended for foodstuffs. It is therefore necessary to provide means for decontaminating the preforms 14.

The invention proposes a method for decontaminating a preform 14 made of thermoplastic material by exposing at least part of the preform 14 to reactive species "RS" obtained by mixing a precursor agent "AP" with a plasma "P". More particularly, they are reactive species that have germicidal properties. The method of decontamination is advantageously applied during handling of the preforms in the plant for making containers, more particularly during transport of the preforms through the manufacturing plant.

The reactive species consist in particular of one or more of the following chemical elements:
reactive oxygen species, also abbreviated to ROS, which include the hydroxyl radical, superoxide anion, hydroxyl ions, the perhydroxyl radical, etc.;
reactive nitrogen species, also abbreviated to RNS, which include in particular nitrogen monoxide (NO);
ozone.

The precursor agent AP is defined as an agent capable of being decomposed into reactive species RS by exposure to a plasma P.

Advantageously, the precursor agent AP is selected so as to decompose completely into reactive species RS so that there is no need to clean the containers 12 at the end of their manufacturing process.

The precursor agent AP is for example formed by hydrogen peroxide ($H_2O_2$), in particular by a solution of hydrogen peroxide and water.

The concentration of hydrogen peroxide in the aqueous solution is for example between 5% and 35%. Hydrogen peroxide and/or water are liable to decompose very quickly into numerous reactive oxygen species (ROS).

Moreover, the reactive species RS obtained by exposure of hydrogen peroxide to a gas in the state of plasma P are stable for a sufficient time to allow decontamination of the preforms 14 throughout their manufacturing process. The reactions between the different reactive species RS are in fact favorable to the promotion of new reactive species RS.

The plasma P is generated by injecting a carrier gas into a reactor 40. The carrier gas is generally dioxygen ($O_2$), and in this case the reactive species RS produced by mixing the plasma P with the precursor agent AP are mainly reactive oxygen species.

As a variant, the carrier gas may also be formed from another pure gas or else from a composition, for example air. When the carrier gas is formed from a gas containing nitrogen, such as air, the plasma comprises reactive nitrogen species and reactive oxygen species. These reactive species react with the precursor agent AP during mixing to form new reactive oxygen species. The reactive species resulting from mixing therefore comprise a mixture of reactive oxygen species and reactive nitrogen species. The reactor 40 makes it possible in this case to generate a cold plasma P obtained at atmospheric pressure. The plasma P is for example obtained by supplying electromagnetic energy to the carrier gas G. For this purpose, the reactor 40 is for example a capacitive reactor 40, which mainly comprises a reaction chamber 42 in which there are two electrodes 44, which are connected electrically to a generator 46 of direct or alternating electric current, allowing a large potential difference to be applied between the two electrodes 44.

According to a first example (not shown), it is a corona effect reactor, in which an electric arc can be created between the two electrodes if a potential difference is applied that is greater than a breakdown voltage between the two electrodes.

According to a second example shown in FIG. 3, it is a dielectric barrier discharge (DBD) reactor 40. In this reactor 40, a barrier 48 made of a dielectric material is interposed between the two electrodes 44. This makes it possible in particular to prevent the production of electric arcs between the two electrodes 44.

It was found that bringing the electrodes 44 into contact with the precursor agent AP was liable to cause premature wear of the electrodes 44 through oxidation.

To solve this problem while keeping the advantages of the production of reactive species RS by plasma P, the invention proposes that mixing of the precursor agent AP with the plasma P should be carried out exclusively outside of the reaction chamber 42 of the reactor 40 before it is in contact with the preform 14. Thus, neither the precursor agent AP, nor the reactive species RS obtained by contact between the precursor agent AP and the plasma P ever come into contact with the electrodes 44. This thus avoids premature corrosion of the electrodes 44.

Furthermore, the fact that the mixture is produced before it is brought into contact with the preform 14 makes it possible to decompose almost all of the precursor agent AP. Thus, the residual content of precursor agent AP in the container 12 made starting from said preform 14 treated in this way is advantageously negligible.

The precursor agent AP is advantageously mixed with the plasma P directly on discharge from the reactor 40. Thus, the bulk of the carrier gas G is still in the state of plasma P at the time of mixing with the precursor agent AP.

To promote the production of reactive species RS, the precursor agent AP is vaporized before it is mixed with the plasma P. Thus, the precursor agent AP is in the vapor state when it is mixed with the plasma P.

As a variant, the precursor agent AP is mixed with the plasma P in the form of mist.

As shown in FIG. 4, the method of the invention thus comprises a first step E1 of production of a plasma P by a reactor 40, then a second step E2 of mixing the precursor agent AP with the plasma P outside of the reactor 40, followed by a third step E3 of spraying the reactive species RS obtained in the second step E2 on the parts of the preform 14 to be decontaminated.

Moreover, the internal and external faces 28, 30 of the preform 14 can also be decontaminated by this method.

However, this method is particularly advantageous for decontaminating the internal face 28 of the preform 14, which is poorly accessible, and its neck 22, which is not heated much by the furnace 32.

In the case of decontamination of the interior of the preform 14, the method comprises advantageously, but not necessarily, a step E4 of confinement of the reactive species RS inside the preform 14 for a time determined counting from their injection, for example less than 12 seconds.

When the reactive species RS are injected into the preform 14 upstream of the heating furnace 32, the defined length of time corresponds to the time taken by the preform 14 to leave the heating furnace 32, for example less than 12 seconds. In this case, confinement of the reactive species RS is carried out by means of the mandrel 39, which will plug the preform 14 during its passage through the heating furnace 32.

This confinement makes it possible to ensure that the reactive species are localized in the place where decontamination is required, and prevent them escaping to the interior of the furnace.

Dispersion of these reactive species could cause oxidation of metal parts present in the furnace.

Moreover, this confinement makes it possible to ensure that the reactive species remain for a certain time in contact with the space delimited by the interior wall of the preform, which guarantees efficacy of the decontamination step.

When the reactive species RS are injected into the preform 14 in another place of the plant, for example downstream of the heating furnace 32, confinement may be carried out by physical plugging of the preform 14 by means of a stopper, or else by projecting a laminar air flow F onto the neck, parallel to the axis of the preform 14 directly toward the interior of the preform 14. The air flow F must then have, in cross section, dimensions greater than those of the neck of the preform 14 to prevent the air flow driving out the reactive species instead of confining them, as is represented by the bundle of parallel arrows F in FIG. 6.

FIG. 3 shows an example of a decontamination device 50 for applying the method of decontamination implemented according to the teachings of the invention.

The decontamination device 50 comprises a decontamination line 52, an upstream end 54 of which is connected to a source 56 of precursor agent AP and a downstream end 58 of which is connected to an injection nozzle 60, which is intended for injecting the reactive species RS onto or into a preform 14. In the example shown, it is a nozzle 60, which is intended to inject the reactive species RS inside the preform 14.

The source 56 of precursor agent AP delivers the precursor agent AP under pressure to allow it to flow to the nozzle 60.

The decontamination device 50 also comprises a reactor 40 of plasma P. The reactor 40 comprises a reaction chamber 42, at least one inlet orifice 62 of which is connected to a source 64 of carrier gas G and an outlet 66 of which is connected to an intermediate section of the decontamination line 52 by a branch pipe 68. The branch pipe 68 splits the decontamination line 52 into an upstream section 52A in which the undecomposed precursor agent AP is intended to circulate, and a downstream section 52B in which the reactive species RS produced by the decomposition of the precursor agent AP when it is mixed with the plasma P are intended to circulate.

The carrier gas G delivered by the source 64 is for example dioxygen or air.

The carrier gas G may be injected under pressure to allow it to flow to the outlet 68.

It is possible to provide a nonreturn valve 70 at the outlet of the reaction chamber 42 to prevent the precursor agent AP or the reactive species RS obtained by decomposition of the precursor agent AP being returned accidentally to the reaction chamber 42. As a variant, when the plasma (P) is generated by injection of the carrier gas into the reactor, the pressure in the reactor is greater than the pressure in the decontamination line (52). Consequently, during application of this method of decontamination, as the pressure in the reactor is greater than the pressure in the decontamination line (52), this avoids any rise of precursor agent (AP) and/or of reactive species in the reactor and thus prevents any oxidation of the latter. For this purpose, advantageously the plasma is generated before and after the step of evaporation of the precursor agent in the decontamination line (52).

The reaction chamber 42 contains two electrodes 44 spaced apart. The electrodes 44 are connected to a generator 46 of electric current. The electrodes 44 are arranged so that the carrier gas G circulating from the inlet orifice 62 to the outlet orifice 66 passes through the space provided between the two electrodes 44. The potential difference applied between the electrodes 44 is sufficient to transform the carrier gas G into plasma P.

Here, it is a reactor 40 with dielectric barrier discharge 48. A barrier 48 of dielectric material is interposed between the two electrodes 44.

When the precursor agent AP is delivered in the liquid state by the source 56 of precursor agent AP, the decontamination line comprises an evaporator 72 of the precursor agent AP, which is arranged upstream of the branch pipe with the reactor 40 of plasma P. The precursor agent AP is for example heated by means of an electric resistance.

As a variant, it is a heat exchanger.

According to another variant of the invention, the evaporator is replaced with a misting device of the precursor agent AP arranged upstream of the branch pipe.

In the example shown in FIG. 1, the decontamination device 50 is arranged for treating the preforms 14 upstream of the furnace 32.

The heat supplied by the furnace in fact makes it possible to accelerate the reactions between the reactive species RS and the microbiological agents present on the surface of the preforms 14. However, it is also possible to arrange the decontamination device 50 in other places of the manufacturing plant 10, for example downstream of the furnace 32.

It was found that decontamination of the interior of the preform 14 was even more effective when the reactive species RS are confined inside the preform 14 after they are injected into the preform 14.

During use of the decontamination device 50, the reactor 40 is supplied with carrier gas G to produce a plasma P of this carrier gas G. The plasma P thus obtained is injected into the decontamination line 52 at the level of the branch pipe 68. Simultaneously, the line 52 is supplied with precursor agent AP, which is vaporized by the evaporator 72. The precursor agent AP thus vaporized is then mixed with the plasma P at the level of the branch pipe, without entering the reactor 40. This mixing activates decomposition of the precursor agent AP into reactive species RS. Then the reactive species RS thus obtained are projected onto the faces to be decontaminated of the preform 14, in this case inside the preform 14 for decontaminating its internal face 28.

When carrying out this method, all of the precursor agent introduced into the decontamination line 52 may be activated completely by the plasma.

In a particular embodiment, it is possible that only part of the precursor agent introduced into the decontamination line 52 is activated by the plasma. In this embodiment, the precursor agent is activated in two complementary ways. There is a first quantity of the precursor agent that is activated directly by the plasma, and the quantity of precursor agent not activated directly is injected into the preform. The quantity of precursor agent not activated directly is injected in vapor form into the preform and will then condense on the interior walls of the body of the preform and will be activated by means of the heating elements, i.e. IR lamps or laser diodes.

The decontamination of the preform by the precursor agent, in particular hydrogen peroxide activated by heating, begins when the precursor agent reaches a certain temperature.

In this embodiment, the method of decontamination comprises two steps of activation of the precursor agent, namely one step of activation by plasma, giving activation of the precursor agent almost instantaneously, i.e. the decontamination of the preform begins as soon as the mixture activated by the plasma is in contact with the preform and in particular the body of the latter. This is followed by a second step of activation of the quantity of precursor agent not activated previously.

Consequently, the kinetics of the two steps of activation is different. The first step of activation has faster reaction kinetics than the reaction kinetics of the second step of activation. Advantageously, depending on the amount of precursor agent injected, it is possible to combine the proportion of the two steps of activation of the precursor agent. This makes it possible to increase the overall kinetics of decontamination of the preform and therefore also its degree of decontamination.

Moreover, having two steps of activation makes it possible to manage the amount of residual precursor agent remaining in the preform at discharge from the furnace, i.e. at the end of decontamination.

The method according to the invention and the device 50 for carrying it out make it possible very advantageously to decontaminate the preforms 14 using a precursor agent AP such as hydrogen peroxide while obtaining a final container with a negligible residual amount of precursor agent AP. Therefore it is not necessary to wash the container 12 at the end of the manufacturing process.

Furthermore, mixing the plasma P with the precursor agent AP makes it possible to obtain a result that is as satisfactory as mixing it inside the reactor, but without causing premature wear of the electrodes 44. Thus, this method is particularly economical as it makes it possible to reduce maintenance work on the reactor 40.

The invention claimed is:

1. A method for decontaminating a preform (14) made of thermoplastic material by exposing at least part of the preform (14) to reactive species (RS) obtained by mixing a precursor agent (AP) with a plasma (P), the plasma (P) being generated by injection of a carrier gas (G) into a reactor (40), the method comprising:
introducing the precursor (AP) into a decontamination line (52) upstream of the reactor (40);
mixing of the precursor agent (AP) with the plasma (P), wherein the mixing is carried out exclusively outside the reactor (40) before it is in contact with the preform (14), wherein the mixing occurs in a branch pipe (68) fluidly connected to the reactor (40) and the decontamination line (52); and
transporting the reactive species (RS) downstream of the branch pipe (68) via the decontamination line (52) to a nozzle, wherein the nozzle is configured to inject the reactive species (RS) onto at least a part of the preform (14).

2. The method as claimed in claim 1, wherein at least one interior face (28) of the preform (14) is exposed to the reactive species (RS), the reactive species (RS) being confined within the preform (14) for a length of time determined by confinement means.

3. The method as claimed in claim 2, wherein the method is carried out while the preform (14) is transported through a container manufacturing plant (10) starting from preforms (14) comprising a furnace (32) for heating the preforms (14), the reactive species (RS) being injected into the preform (14) before or during its heating in the heating furnace (32), the reactive species (RS) being confined in the preform (14) up to its discharge from the heating furnace (32).

4. The method as claimed in claim 3, wherein the reactive species (RS) are confined in the preform (14) by means of a mandrel (39), which grips the preform (14) by its neck to allow it to be moved in the heating furnace (32).

5. The method as claimed in claim 1, wherein the precursor agent (AP) comprises hydrogen peroxide.

6. The method as claimed in claim 1, wherein the precursor agent (AP) is in the vapor state when it is mixed with the plasma (P).

7. The method as claimed in claim 1, wherein the precursor agent (AP) is in the form of mist when it is mixed with the plasma (P).

8. The method as claimed in claim 1, wherein the carrier gas (G) is formed by dioxygen.

9. The method as claimed in claim 1, wherein the carrier gas (G) is air.

10. The method as claimed in claim 1, wherein the reactive species comprise one or more of the following chemical elements:
   reactive oxygen species (ROS);
   reactive nitrogen species (RNS);
   ozone ($O_3$).

11. A decontamination device (50) for carrying out the method implemented in claim 1, the device comprising:
   a decontamination line (52), an upstream end of which is connected to a source (56) of precursor agent (AP) and a downstream end of which is connected to at least one injection nozzle (60) intended for projecting, onto at least part of the preform (14), the reactive species (RS) obtained by decomposition of the precursor agent (AP) when it is mixed with the plasma (P); and
   a plasma reactor (40) comprising a reaction chamber (42) having two electrodes (44) therewithin, wherein the plasma reactor is connected to a source (64) of carrier gas (G) and an outlet (66) of which is connected to the decontamination line (52) by a branch pipe (68), which splits the decontamination line (52) into an upstream section (52A) in which undecomposed precursor agent (AP) is intended to circulate, and a downstream section (52B) in which the reactive species (RS) produced by the decomposition of the precursor agent (AP) when it is mixed with the plasma (P) are intended to circulate, wherein the mixing occurs in the downstream section outside of the reaction chamber, and wherein neither the precursor agent (AP) nor the reactive species (RS) contact the electrodes (44).

12. The device (50) as claimed in claim 11, wherein the plasma reactor (40) is a cold plasma reactor such as a corona discharge reactor or a dielectric barrier discharge reactor.

13. The device (50) as claimed in claim 11, wherein the decontamination line (52) comprises an evaporator (72) of the precursor agent (AP) which is arranged upstream of the branch pipe (68) with the plasma reactor (40).

14. The device (50) as claimed in claim 11, wherein the decontamination line (52) comprises a misting device of the precursor agent (AP), which is arranged upstream of the branch pipe (68).

15. The device (50) as claimed in claim 11, further comprising a nonreturn valve at the outlet (66) that prevents a return to the reaction chamber (42) of the precursor agent (AP) and the reactive species (RS).

16. The device (50) as claimed in claim 11, wherein reaction chamber (42) comprises a higher pressure than the decontamination line (52) to prevent a return to the reaction chamber (42) of the precursor agent (AP) or the reactive species (RS).

* * * * *